(12) United States Patent
Longsworth

(10) Patent No.: US 7,264,602 B1
(45) Date of Patent: Sep. 4, 2007

(54) BANDAGE ASSEMBLY

(76) Inventor: Sheryl M. Longsworth, 10748 Olson Dr., Rancho Cordova, CA (US) 95670

( * ) Notice: Subject to any disclaimer, the term of this patent is extended or adjusted under 35 U.S.C. 154(b) by 0 days.

(21) Appl. No.: 11/427,124

(22) Filed: Jun. 28, 2006

(51) Int. Cl.
A61F 13/00 (2006.01)

(52) U.S. Cl. .............. 602/2; 607/112; 602/41; 602/59

(58) Field of Classification Search .......... 602/2; 607/96, 108–112
See application file for complete search history.

(56) References Cited

U.S. PATENT DOCUMENTS

| 3,885,403 | A | * | 5/1975 | Spencer | ............ 62/530 |
| 4,055,188 | A | | 10/1977 | Pelton | |
| 4,347,848 | A | | 9/1982 | Hubbard et al. | |
| 4,676,247 | A | | 6/1987 | Van Cleve | |
| 5,431,622 | A | * | 7/1995 | Pyrozyk et al. | ............ 602/2 |
| 5,514,170 | A | | 5/1996 | Mauch | |
| 5,887,437 | A | * | 3/1999 | Maxim | ............ 62/4 |

* cited by examiner

Primary Examiner—Kim M. Lewis

(57) ABSTRACT

A bandage assembly includes a panel that is flexible and has a first end edge, a second edge, a first lateral edge and a second lateral edge. The panel has a first side and a second side. An adhesive is attached to and covers the second side of the panel. A housing has a gel therein and defines a gel pack. The gel pack is attached to a central portion of the second side of the panel. The gel pack is positioned between the first and second end edges. The gel is selectively cooled. The panel may be attached to a portion of skin and the gel pack aligned with a wound.

1 Claim, 2 Drawing Sheets

BANDAGE ASSEMBLY

BACKGROUND OF THE INVENTION

1. Field of the Invention

The present invention relates to bandage devices and more particularly pertains to a new bandage device for covering a wound and which may be used for selectively cooling an area.

2. Description of the Prior Art

The use of bandage devices is known in the prior art. While these devices fulfill their respective, particular objectives and requirements, the need remains for a device that also cools an area being covered by a bandage. For this reason, the device should include a cooling member in conjunction with a more common bandage device. Further, the cooling member should be removable from the bandage device so that it may be used without an adhesive portion of the bandage device.

SUMMARY OF THE INVENTION

The present invention meets the needs presented above by generally comprising a panel that is flexible and has a first end edge, a second edge, a first lateral edge and a second lateral edge. The panel has a first side and a second side. An adhesive is attached to and covers the second side of the panel. A housing has a gel therein and defines a gel pack. The gel pack is attached to a central portion of the second side of the panel. The gel pack is positioned between the first and second end edges. The gel is selectively cooled. The panel may be attached to a portion of skin and the gel pack aligned with a wound.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
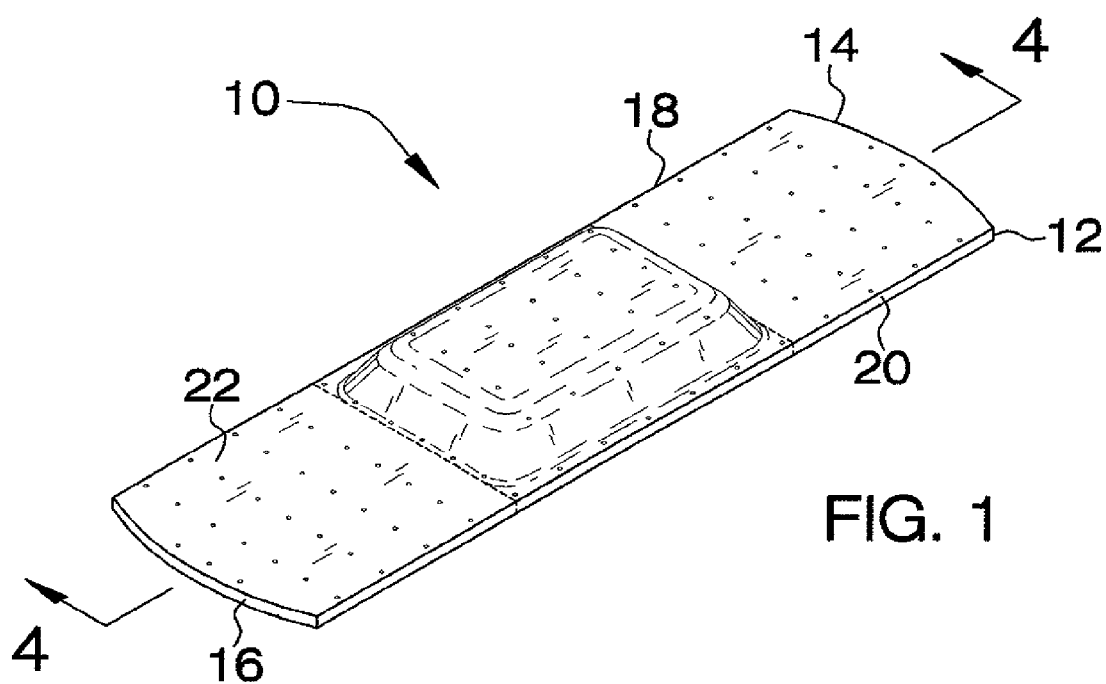
FIG. 1 is a top perspective view of a bandage assembly according to the present invention.
Figure 2:
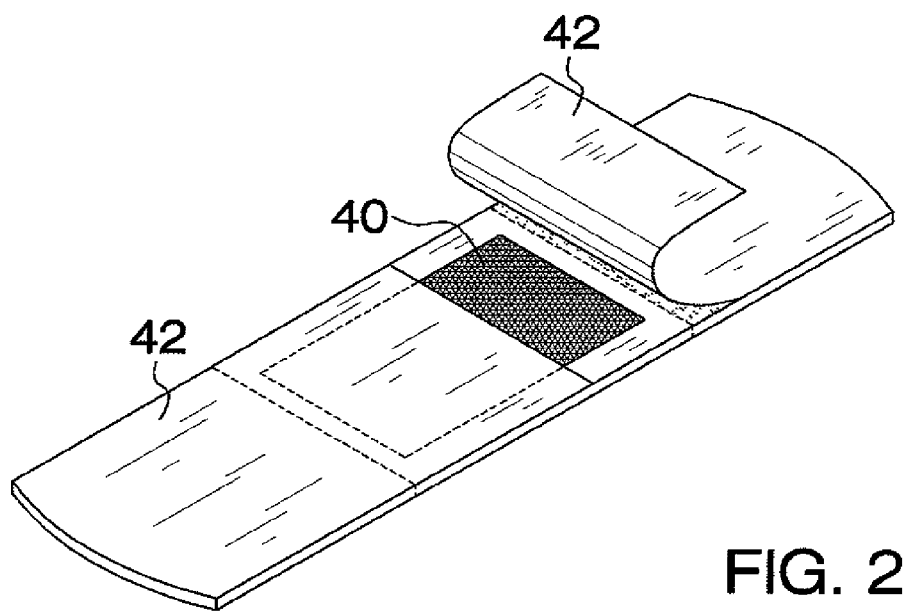
FIG. 2 is a bottom perspective view of the present invention.
Figure 3:
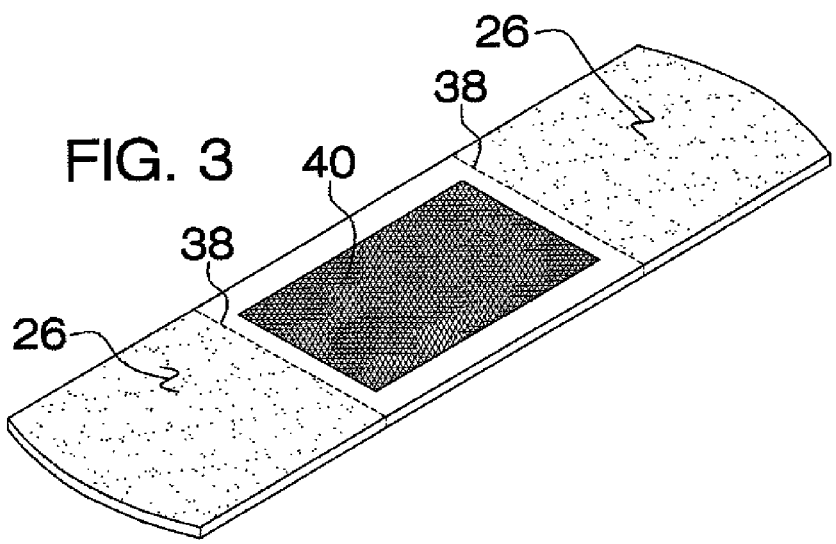
FIG. 3 is a bottom perspective view of the present invention with a covering removed.
Figure 4:
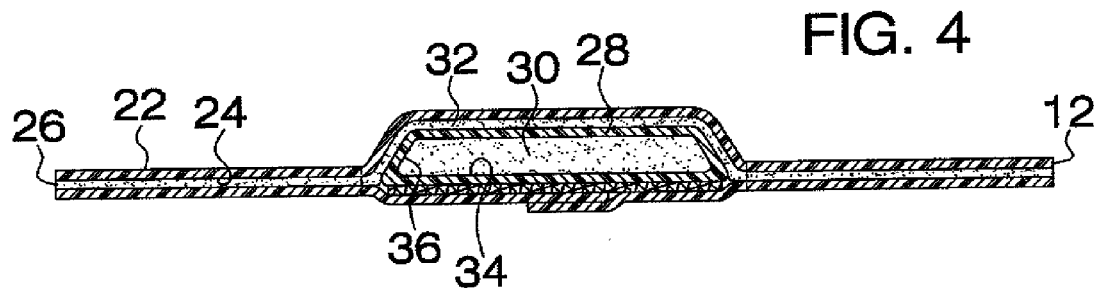
FIG. 4 is a cross-sectional view taken along line 4-4 of FIG. 1 of the present invention.
Figure 5:
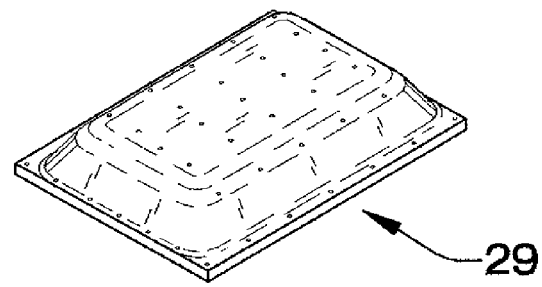
FIG. 5 is a top perspective view of the present invention.

With reference now to the drawings, and in particular to FIGS. 1 through 5 thereof, a new bandage device embodying the principles and concepts of the present invention and generally designated by the reference numeral 10 will be described.

As best illustrated in FIGS. 1 through 5, the bandage assembly 10 generally comprises a panel 12 that is flexible and has a first end edge 14, a second edge 16, a first lateral edge 18 and a second lateral edge 20. The panel 12 has a first side 22 and a second side 24 and may be comprised of a cloth material. An adhesive 26 is attached to and covers the second side 22 of the panel 12.

A housing 28 has a gel 30 therein and defines a gel pack 29. The gel pack 30 is attached to a central portion of the second side 24 of the panel 12 and is secured to the panel 12 with the adhesive 26. The gel pack 29 is positioned between the first 14 and second 16 end edges. The gel pack 29 substantially extends from the first lateral edge 18 to the second lateral edge 20. The housing 28 has a top wall 32, a bottom wall 34 and a perimeter wall 36 extending between the top 32 and bottom 34 walls. The perimeter wall 36 is angled outwardly from said top wall 32 to said bottom wall 34. The panel 12 is coextensive with and is attached to the top 32 and the peripheral 36 walls. The housing 28 is comprised of a flexible material. The gel 29 is selectively cooled and may be brought to a temperature below 0° C. The panel 12 is perforated 38 adjacent to the housing 28. This allows a portion of the panel 12 that is attached to the housing 28 to be removed from portions of the panel 12 not attached to the housing 28. The housing 28 may then be used without being attached to the skin with the adhesive 26.

An absorbent material 40 is attached to a bottom side of the housing 28. The housing 28 is positioned between the panel 12 and the absorbent material 40. The absorbent material 40 may be comprised of any conventional absorbent material used for bandages. A covering 42 is removably attached to and covers the adhesive 26, and also covers the absorbent material 40. The covering 42 has a coating thereon, such as wax, so that the covering 42 may be easily removed from the adhesive. The covering 42 may be divided into a pair of coverings.

In use, the panel 12 may be attached to a portion of skin and the absorbent material 40 may be used as a conventional wound cover. The gel pack 29 is aligned with the wound so that its cooling affects may be utilized. The gel 30 may be of the type required to be cooled before use. Alternatively, the housing 28 may include a gel 30 comprising chemicals that produce an endothermic reaction when mixed.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A bandage assembly comprising:
   a panel being flexible and having a first end edge, a second edge, a first lateral edge and a second lateral edge, said panel having a first side and a second side, said panel comprising a cloth material;

an adhesive being attached to and covering said second side of said panel;

a housing having a gel therein and defining a gel pack, said get pack being attached to a central portion of said second side of said panel and being secured to said panel with said adhesive, said gel pack being positioned between said first and second end edges, said gel pack substantially extending from said fast lateral edge to said second lateral edge, said housing having a top wall, a bottom wall and a perimeter wall extending between said top and bottom walls, said panel being coextensive with and being attached to said top and said peripheral walls, said housing being comprised of a flexible material, said gel being selectively cooled, said panel being perforated adjacent to said housing, wherein a portion of said panel attached to said housing is removable from a portion of said panel not attached to said housing at the perforations;

an absorbent material being attached to a bottom side of said housing, said housing being positioned between said panel and said absorbent material;

a covering being removably attached to and covering said adhesive; and wherein said panel may be attached to a portion of skin and said gel pack aligned with a wound.

\* \* \* \* \*